US00PP36755P2

(12) United States Plant Patent
Mathey

(10) Patent No.: US PP36,755 P2
(45) Date of Patent: Jun. 24, 2025

(54) ***PRUNUS* PLANT NAMED 'SMNPJL'**

(50) Latin Name: ***Prunus japonica* X *Prunus jacquemontii***
Varietal Denomination: SMNPJL

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 18/947,700

(22) Filed: Nov. 14, 2024

(51) Int. Cl.
*A01H 5/08* (2018.01)
*A01H 6/74* (2018.01)

(52) U.S. Cl.
USPC ..... Plt./182
CPC ..... *A01H 6/7427* (2018.05)

(58) Field of Classification Search
USPC ..... Plt./181, 182, 156, 263.1, 226
CPC ..... A01H 5/0837; A01H 5/085
See application file for complete search history.

*Primary Examiner* — Kent L Bell
(74) *Attorney, Agent, or Firm* — C. Anne Whealy

(57) ABSTRACT

A new and distinct cultivar of *Prunus* plant named 'SMNPJL', characterized by its relatively compact, upright to outwardly spreading plant habit; vigorous growth habit and moderate growth rate; freely branching habit; dense and bushy appearance; freely flowering habit; light pink-colored flowers with darker pink-colored marginal edges; high fruit yield per plant; and cherry red-colored fruits that are tart to slightly sweet in flavor.

3 Drawing Sheets

Figure 1:
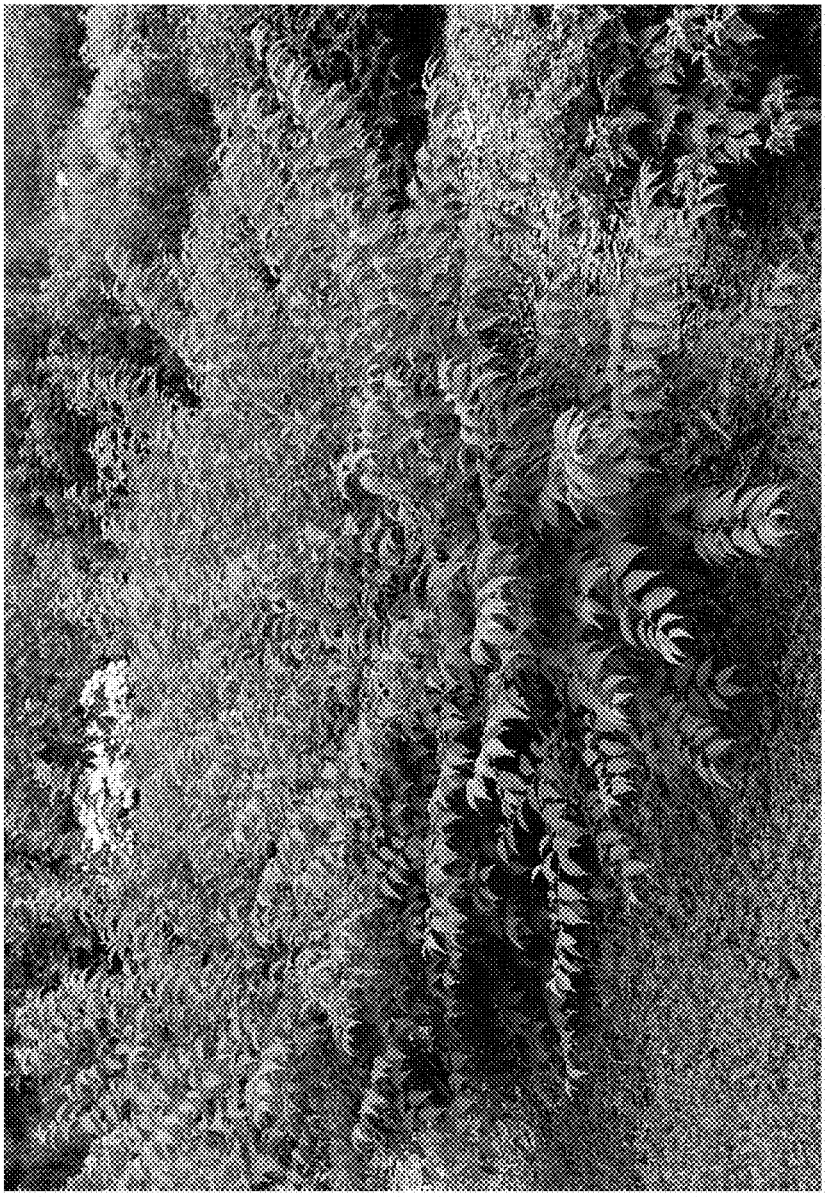

Botanical designation: *Prunus japonica* X *Prunus jacquemontii*.

Cultivar denomination: 'SMNPJL'.

BACKGROUND OF THE INVENTION

The present invention relates to a new and distinct cultivar of *Prunus* plant, botanically known as *Prunus japonica* X *Prunus jacquemontii*, commonly referred to as Bush Cherry and hereinafter referred to by the cultivar name 'SMNPJL'.

The new *Prunus* is a product of a planned breeding program conducted by the Inventor in Grand Haven, Michigan. The objective of the breeding program was to develop new compact, freely branching and freely flowering *Prunus* plants with high fruit yield.

The new *Prunus* plant originated from an open-pollination during the summer of 2016 in Grand Haven, Michigan of *Prunus japonica* X *Prunus jacquemontii* 'Joel', not patented, as the female, or seed, parent with an unknown selection of *Prunus japonica* X *Prunus jacquemontii* as the male, or pollen, parent. The new *Prunus* plant was discovered and selected by the Inventor during the summer of 2019 as a single flowering plant within the progeny of the stated open-pollination in a controlled environment in Grand Haven, Michigan.

Asexual reproduction of the new *Prunus* plant by softwood stem cuttings in a controlled greenhouse environment in Grand Haven, Michigan since the summer of 2019 has shown that the unique features of this new *Prunus* plant are stable and reproduced true to type in successive generations of asexual reproduction.

SUMMARY OF THE INVENTION

Plants of the new *Prunus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNPJL'. These characteristics in combination distinguish 'SMNPJL' as a new and distinct *Prunus* plant:

1. Relatively compact, upright to outwardly spreading plant habit.
2. Vigorous growth habit and moderate growth rate.
3. Freely branching habit; dense and bushy appearance.
4. Freely flowering habit.
5. Light pink-colored flowers with darker pink-colored marginal edges.
6. High fruit yield per plant.
7. Cherry red-colored fruits that are tart to slightly sweet in flavor.

Plants of the new *Prunus* can be compared to plants of the female parent, 'Joel'. In side-by-side comparisons, plants of the new *Prunus* differ primarily from plants of 'Joel' in the following characteristics:

1. Plants of the new *Prunus* are more compact than plants of 'Joel'.
2. Plants of the new *Prunus* are more freely branching and denser than and not as rangy and open as plants of 'Joel'.
3. Plants of the new *Prunus* produce more fruit per plant than plants of 'Joel'.

Plants of the new *Prunus* can be compared to plants of *Prunus japonica* X *Prunus jacquemontii* 'Jan', not patented. In side-by-side comparisons, plants of the new *Prunus* differ primarily from plants of 'Jan' in the following characteristics:

1. Plants of the new *Prunus* are larger than plants of 'Jan'.
2. Plants of the new *Prunus* are more freely branching and denser than and not as rangy and open as plants of 'Jan'.
3. Plants of the new *Prunus* produce more fruit per plant than plants of 'Jan'.

BRIEF DESCRIPTION OF THE PHOTOGRAPHS

The accompanying colored photographs illustrate the overall appearance of the new *Prunus* plant showing the colors as true as it is reasonably possible to obtain in colored reproductions of this type. Colors in the photographs may differ slightly from the color values cited in the detailed botanical description which accurately describe the colors of the new *Prunus* plant.

The photograph on the first sheet (FIG. 1) is a side perspective view of a typical vegetative plant of 'SMNPJL' grown in an outdoor nursery.

Figure 2:
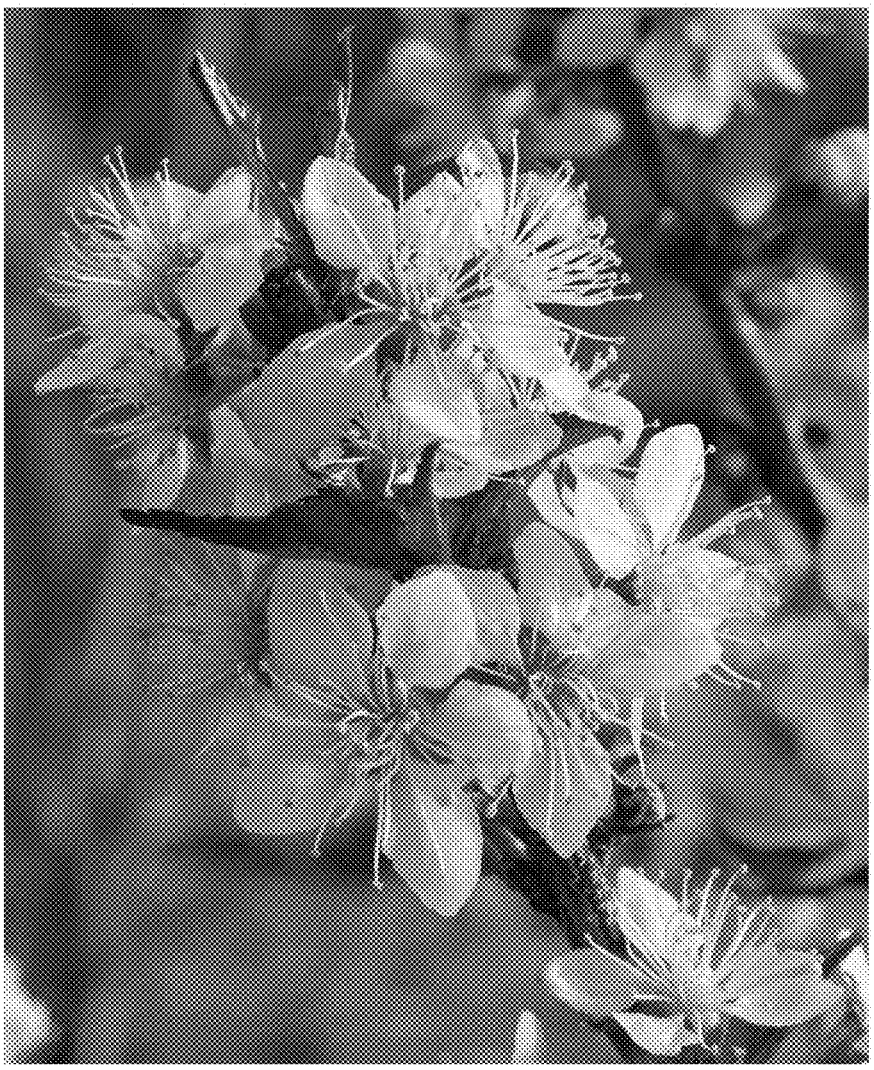

The photograph on the second sheet (FIG. 2) is a close-up view of typical flowers 'SMNPJL'.

Figure 3:
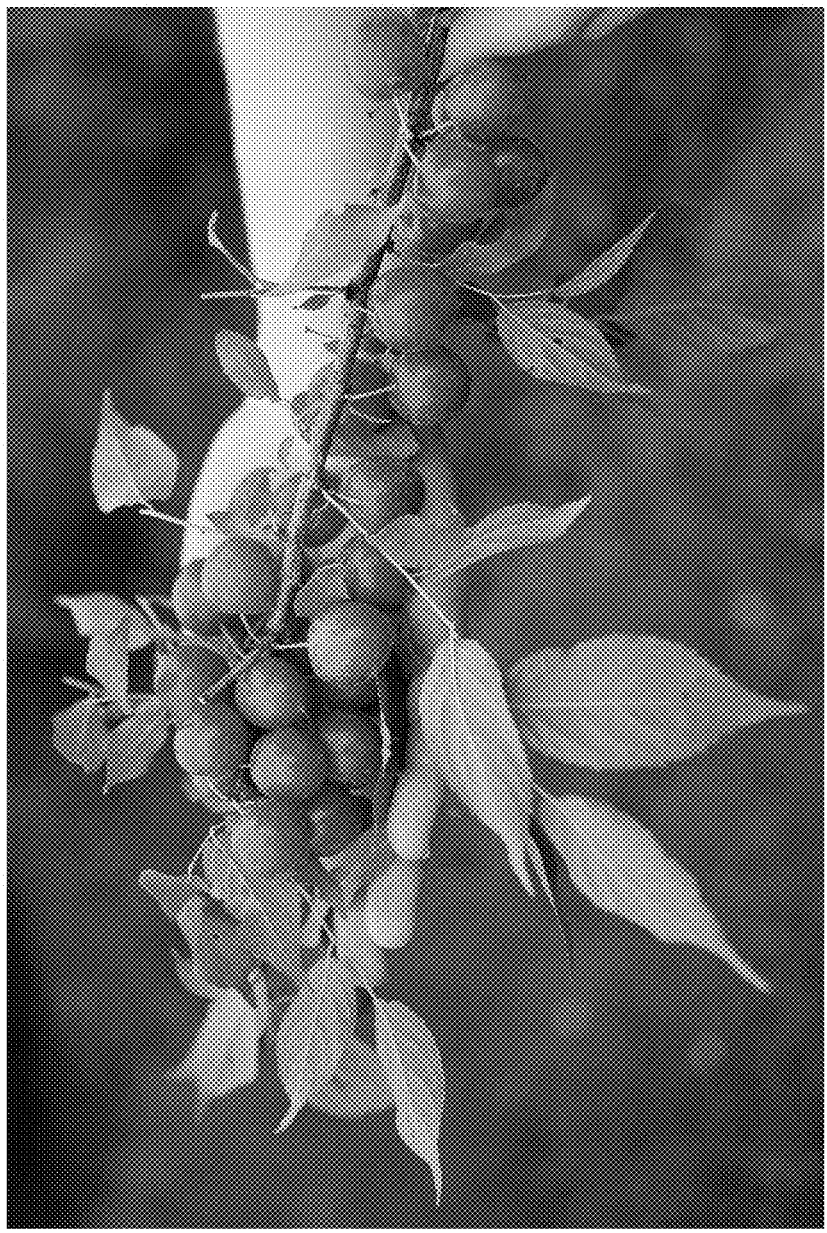

The photograph on the third sheet (FIG. 3) is close-up view of typical fruits of 'SMNPJL'.

DETAILED BOTANICAL DESCRIPTION

The following observations, measurements and values describe plants grown in the late spring and early summer in three-gallon containers in a polyethylene-covered greenhouse in Grand Haven, Michigan and under cultural practices typical of commercial *Prunus* production. During the production of the plants, day temperatures ranged from 18° C. to 27° C. and night temperatures ranged from 5° C. to 10° C. Plants were five years old when the photographs were taken and three years old with the detailed description was taken. In the description, color references are made to The Royal Horticultural Society Colour Chart, 2015 Edition, except where general terms of ordinary dictionary significance are used.

Botanical classification: *Prunus japonica* X *Prunus jacquemontii* 'SMNPJL'.

Parentage:

*Female, or seed, parent.*—*Prunus japonica* X *Prunus jacquemontii* 'Joel', not patented.

*Male, or pollen, parent.*—Unknown selection of *Prunus japonica* X *Prunus jacquemontii*, not patented.

Propagation:

*Type.*—By softwood stem cuttings.

*Time to initiate roots, summer.*—About 18 days at temperatures ranging from about 18° C. to 27° C.

*Time to produce a rooted young plant, summer.*—About 30 days at temperatures ranging from about 18° C. to 27° C.

*Root description.*—Thin to medium in thickness; fleshy and fibrous; typically brown in color, actual color of the roots is dependent on substrate composition, water quality, fertilizer, substrate temperature and physiological age of roots.

*Rooting habit.*—Freely branching; dense.

Plant description:

*Plant form and growth habit.*—Perennial deciduous shrub; relatively compact, upright to outwardly spreading plant habit; vigorous growth habit and rapid growth rate.

*Branching habit.*—Freely branching habit; dense and bushy appearance with about four primary lateral branches each with about 20 to 40 secondary lateral branches developing per plant; pinching will enhance lateral branch development.

*Plant height.*—About 110 cm.

*Plant diameter* (*area of spread*).—About 140 cm.

Lateral branch description:

*Length, primary branches.*—About 92.6 cm.

*Diameter, primary branches.*—About 1.6 cm.

*Length, secondary branches.*—About 48.5 cm.

*Diameter, secondary branches.*—About 2 cm.

*Internode length.*—About 2 cm.

*Aspect.*—About 20° to 80° from vertical.

*Strength.*—Strong.

*Texture.*—Smooth, glabrous; becoming woody with development.

*Color, developing, upper surface.*—Close to 144C slightly tinged with close to 174A.

*Color, developing, lower surface.*—Close to 144C.

*Color, when woody, upper and lower surfaces.*—Close to 201B.

Leaf description:

*Arrangement.*—Alternate, simple.

*Length.*—About 4.5 cm.

*Width.*—About 2.5 cm.

*Shape.*—Elliptic.

*Apex.*—Abruptly acuminate.

*Base.*—Obtuse, rounded.

*Margin.*—Doubly serrate.

*Texture, upper surface.*—Smooth, glabrous.

*Texture, lower surface.*—Smooth, glabrous with prominent venation.

*Venation pattern.*—Pinnate.

*Color.*—Developing leaves, upper and lower surfaces: Close to 144A. Fully expanded leaves, upper surface: Close to NN137A; venation, close to 144C. Fully expanded leaves, lower surface: Close to 147B; venation, close to 144C.

*Petioles.*—Length: About 5 mm. Diameter: About 1 mm. Texture, upper and lower surfaces: Smooth, glabrous. Color, upper surface: Close to 144C slightly tinged with close to 174C. Color, lower surface: Close to 144C.

Flower description:

*Flower appearance and arrangement.*—Single stellate axillary flowers; freely flowering habit with about 184 developing and open flowers per secondary lateral branch and numerous flowers developing per plant during the flowering season; flowers face upright to outwardly.

*Fragrance.*—None detected.

*Natural flowering season.*—Plants flower in March and April in Michigan.

*Flower longevity.*—Individual flowers last about one week on the plant; flowers not persistent.

*Flower buds.*—Length: About 5 mm. Diameter: About 3 mm. Shape: Spatulate. Color: Close to 62C to 62D.

*Flower diameter.*—About 1.5 cm.

*Flower length.*—About 5 mm.

*Petals.*—Quantity and arrangement: Five in a single whorl. Length: About 6 mm. Width: About 4 mm. Shape: Elliptic. Apex: Obtuse. Base: Attenuate. Margin: Entire. Texture, upper and lower surfaces: Smooth, soft; glabrous. Color: When opening, upper and lower surfaces: Close to 69B; marginal edges, blushed with close to 68B. Fully opened, upper and lower surfaces: Close to 69D; marginal edges, blushed with close to 68B.

*Sepals*.—Quantity and arrangement: Five in a single whorl fused at the base into a stellate-shaped calyx. Length: About 3 mm. Width: About 1.5 mm. Shape: Linear to narrowly deltoid; recurved. Apex: Broadly acute. Margin: Entire. Texture, upper and lower surfaces: Smooth, glabrous. Color, upper and lower surfaces: Close to 144A.

*Peduncles*.—Length: About 4 mm. Diameter: About 1 mm. Aspect: About 20° to 45° from the stem axis. Strength: Strong; somewhat flexible. Texture: Smooth, glabrous. Color, upper and lower surfaces: Close to 144A.

*Reproductive organs*.—Stamens: Quantity per flower: About 30 to 40. Filament length: About 6 mm. Filament color: Close to NN155B. Anther length: Less than 1 mm. Anther shape: Globose. Anther color: Close to 162B. Pollen amount: Moderate. Pollen color: Close to 162B. Pistils: Quantity per flower: One. Pistil length: About 8 mm. Stigma color: Close to 144A. Style length: About 8 mm. Style color: Close to 144A. Ovary color: Close to 144A. Fruits: Quantity per lateral branch: About 20 to 40 with numerous fruits developing per plant. Length: About 2.5 cm. Diameter: About 2 cm. Shape: Spherical. Taste: Tart to slightly sweet. Color: Close to 42B. Seeds: Quantity per fruit: One. Length: About 1.1 cm. Diameter: About 8 mm. Color: Close to 165B.

Garden performance: Plants of the new *Prunus* have been observed to have good garden performance and tolerate rain, wind and to be suitable for USDA Hardiness Zones 3 through 8.

Pathogen & pest resistance: To date, plants of the new *Prunus* have not been shown to be resistant to pathogens and pests common to *Prunus* plants.

It is claimed:

1. A new and distinct *Prunus* plant named 'SMNPJL' as herein illustrated and described.

* * * * *